(12) United States Patent
Fairs et al.

(10) Patent No.: US 8,327,724 B2
(45) Date of Patent: Dec. 11, 2012

(54) SAMPLE PREPARATION APPARATUS

(75) Inventors: Michael Roy Fairs, Kempston (GB); Thomas David Ford, Royston (GB); Piers Sebastian Harding, Buckworth (GB); Gary Stephen Howard, Swavesey (GB); Barry Boyes, Edgewood, MD (US); John Walter Czajka, Edgewood, MD (US); Douglas Jason Green, Edgewood, MD (US); Jay Lewington, Bisley (GB); Carmelo Volpe, Cheshunt (GB); Colin Fewster, Abbotts Langley (GB); Jason Betley, Lackford (GB); Catherine Mills, London (GB); William Richard Mawer, Welwyn (GB)

(73) Assignee: Smiths Detection-Watford Limited, Watford (GB)

( * ) Notice: Subject to any disclaimer, the term of this patent is extended or adjusted under 35 U.S.C. 154(b) by 86 days.

(21) Appl. No.: 12/449,855

(22) PCT Filed: Feb. 28, 2008

(86) PCT No.: PCT/GB2008/000662
§ 371 (c)(1),
(2), (4) Date: Mar. 22, 2010

(87) PCT Pub. No.: WO2008/107639
PCT Pub. Date: Sep. 12, 2008

(65) Prior Publication Data
US 2010/0192706 A1 Aug. 5, 2010

(30) Foreign Application Priority Data
Mar. 2, 2007 (GB) .................................. 0704035.5

(51) Int. Cl.
*G01N 1/00* (2006.01)
(52) U.S. Cl. ......................................................... 73/863
(58) Field of Classification Search ....................... None
See application file for complete search history.

(56) References Cited

U.S. PATENT DOCUMENTS

| 4,734,260 | A | * | 3/1988 | Lautenschlager | 356/409 |
|---|---|---|---|---|---|
| 5,043,141 | A | * | 8/1991 | Wilson et al. | 422/52 |
| 6,333,088 | B1 | * | 12/2001 | Le Febre et al. | 428/36.91 |
| 7,482,143 | B2 | | 1/2009 | Ammann et al. | |
| 7,524,652 | B2 | | 4/2009 | Ammann et al. | |
| 7,560,255 | B2 | | 7/2009 | Ammann et al. | |
| 7,560,256 | B2 | | 7/2009 | Ammann et al. | |
| 2002/0197631 | A1 | | 12/2002 | Lawrence et al. | |
| 2004/0005608 | A1 | | 1/2004 | Saghbini et al. | |
| 2004/0076546 | A1 | * | 4/2004 | Bissett | 422/68.1 |

(Continued)

FOREIGN PATENT DOCUMENTS

EP        1 614 470 B1        1/2006

(Continued)

*Primary Examiner* — Robert R Raevis

(57) ABSTRACT

Apparatus for preparing a biological sample for PCR analysis has an inlet (4) for receiving the sample (15) and a sieve (13) through which the sample is forced by screwing down an inlet cap (16). A lysis solution between two rupturable seals (11 and 12) is effective to disrupt the cells of the sample and release nucleic acid. The apparatus is mounted releasably on a PCR machine (2) having a motor (2') releasably coupled with a drive mechanism (3, 36, 40) in the apparatus to effect a rotary and a vertical up and down movement of its components (30, 31, 32, 42). The apparatus has a transparent cuvette (5) and a needle (71) extending to the lower end of the cuvette, by which the prepared sample is dispensed to the cuvette for PCR analysis.

15 Claims, 9 Drawing Sheets

U.S. PATENT DOCUMENTS

2005/0064582 A1  3/2005  Wittwer et al.

FOREIGN PATENT DOCUMENTS

| EP | 1 623 764 B1 | 2/2006 |
| EP | 1 383 602 B1 | 6/2006 |
| WO | WO 2005/019836 A2 | 3/2005 |
| WO | WO 2005/085800 A1 | 9/2005 |
| WO | WO 2005/106040 A2 | 11/2005 |
| WO | WO 2005/121963 A2 | 12/2005 |
| WO | WO 2006/079814 A2 | 8/2006 |
| WO | WO 2006/090180 A1 | 8/2006 |

* cited by examiner

Fig.3A.
Fig.3B.
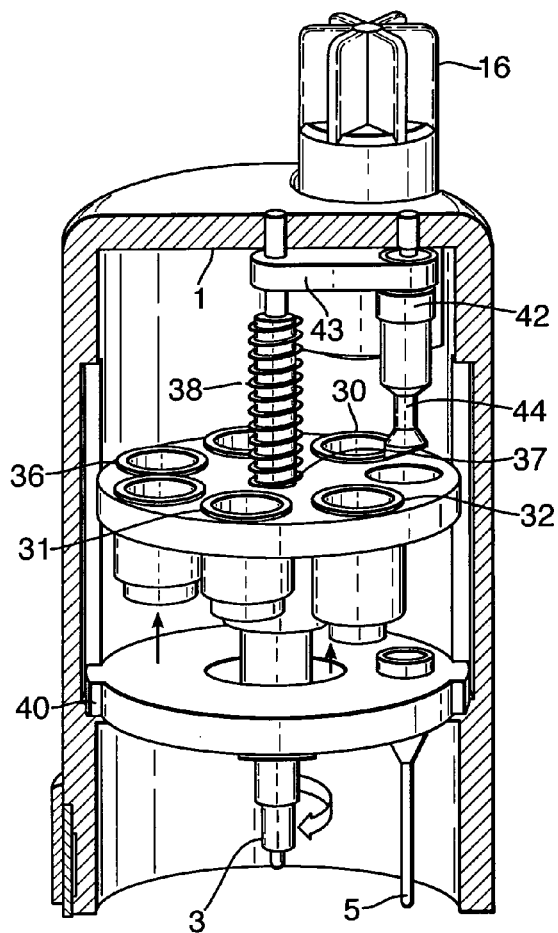
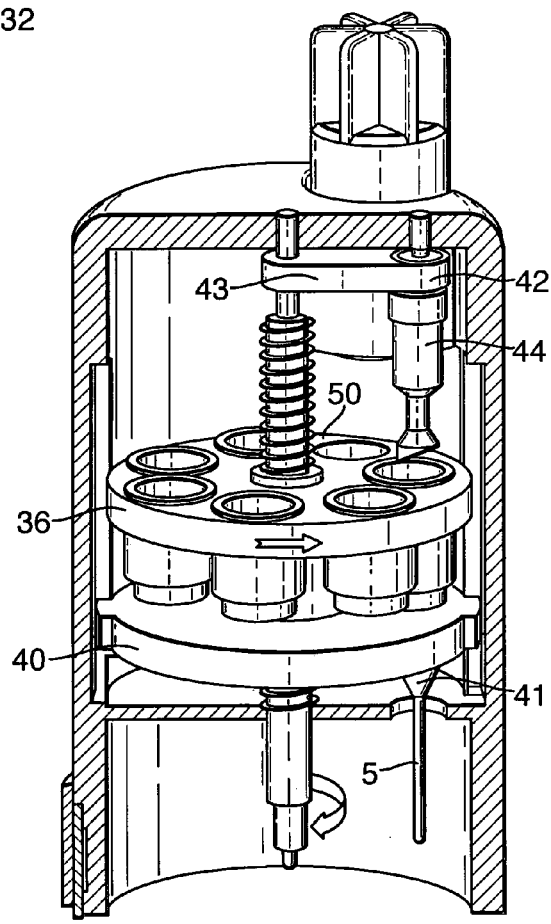

SAMPLE PREPARATION APPARATUS

This invention relates to sample preparation apparatus having an inlet opening by which fluid and semi-solid sample material can be added to the apparatus, the inlet having a recess for receiving the sample material.

The invention is more particularly, but not exclusively, concerned with apparatus for preparing samples containing nucleic acid, such as DNA or RNA, into a form suitable for amplification by PCR techniques, detection and analysis.

Conventional techniques for preparing samples for PCR analysis involve manually treating the sample and transferring it between different containers containing different treatment solutions. These techniques require skilled operatives and are difficult to perform in the field. There are many situations where it is desirable to be able to perform a rapid DNA analysis or the like on a sample in the vicinity where the sample has been taken, such as for medical, veterinary or agricultural applications. Portable DNA analysis equipment (such as the Bio-Seeq sold by Smiths Detection—Watford Limited) is available, which can be used easily with little training. However, the difficulty of preparing the sample limits the number of applications in which such equipment can be used. Examples of preparation apparatus are described in WO05/121963, WO06/090180, WO06/079814, EP1383602, WO05/106040 and WO05/019836.

It is an object of the present invention to provide alternative sample preparation apparatus.

According to one aspect of the present invention there is provided sample preparation apparatus of the above-specified kind, characterised in that a sieve member extends across the recess, and that the apparatus includes a maceration member having a portion adapted to extend into an upper part of the recess such that by displacing the maceration member rotationally and downwardly semi-solid sample material is pushed through the sieve member and macerated.

The maceration member may be in the form of a cap adapted to close the inlet. The maceration member and the inlet are preferably provided with cooperating screw threads so that as the maceration member is screwed onto the inlet it contacts the sample material and forces it through the sieve member. The recess may contain a substance effective to disrupt the cells of the sample material and release nucleic acid. The substance may include a lysis solution. The substance may be contained between two rupturable seals that are broken as the maceration member is displaced inwardly. The apparatus may be arranged to prepare a biological sample from the macerated fluid or semi-solid sample material and to dispense it into an elongate transparent cuvette suitable for PCR amplification and analysis, the cuvette having an open upper end and a closed lower end, the apparatus including a needle extending into the lower end of the cuvette such as to provide clearance between the outside of the needle and the inside of the cuvette, and the apparatus being arranged to dispense the PCR sample into the upper end of the needle so that it fills the cuvette from its lower end.

According to another aspect of the present invention there is provided a PCR analysis system comprising a PCR amplification and analysis machine and a sample preparation apparatus according to the above one aspect of the invention.

The sample preparation apparatus is preferably removably mounted with the PCR machine, the sample preparation apparatus having a drive mechanism for displacing components within it, and the PCR machine including a motor arrangement releasably coupled with the drive mechanism such that the motor arrangement provides motive power to displace the components in the sample preparation apparatus.

The motor arrangement may be arranged to effect both rotary and vertical up and down movement of components within the sample preparation apparatus.

According to a further aspect of the present invention there is provided sample preparation apparatus for preparing a biological sample and dispensing it into an elongate transparent cuvette suitable for PCR amplification and analysis, characterised in that the cuvette has an open upper end and a closed lower end, that the apparatus includes a needle extending into the lower end of the cuvette such as to provide clearance between the outside of the needle and the inside of the cuvette, and that the apparatus is arranged to dispense the PCR sample into the upper end of the needle so that it fills the cuvette from its lower end.

According to a fourth aspect of the present invention there is provided a PCR analysis system comprising a PCR amplification and analysis machine and sample preparation apparatus, characterised in that the sample preparation apparatus is removably mounted with the PCR machine, that the sample preparation apparatus has a drive mechanism for displacing components within it, and that the PCR machine includes a motor arrangement releasably coupled with the drive mechanism such that the motor arrangement provides motive power to displace the components in the sample preparation apparatus.

Preparation apparatus for samples containing nucleic acid, according to the present invention, will now be described, by way of example, with reference to the accompanying drawings, in which:

FIGS. 3A and 3B are partly cut-away views of the apparatus at two different stages of operation;

Figure 1:
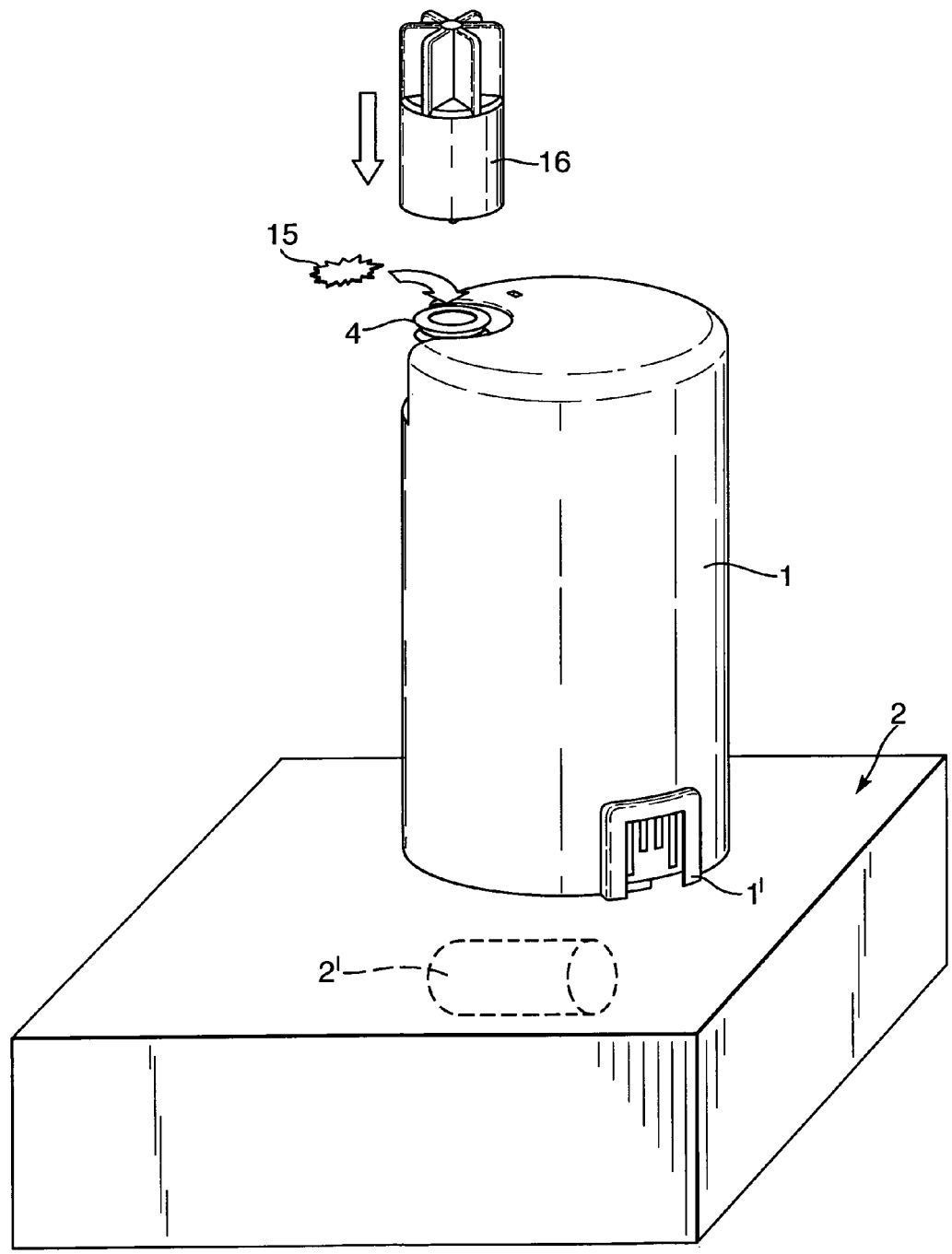
FIG. 1 is a perspective view of the apparatus.

With reference first to FIGS. 1 and 3 there is shown sample preparation apparatus for preparing a solid or semi-solid sample into a form suitable for nucleic acid analysis. The apparatus has a cylindrical casing 1 with a height of about 200 mm, a diameter of about 120 mm. The apparatus in use is mounted directly on a PCR analysis machine, indicated generally by the numeral 2, in a vertical orientation by means of a coupling 1' at its lower end. The PCR machine 2 has a motor 2' that connects with a drive shaft 3 (FIGS. 3A and 3B) extending axially, centrally within the preparation apparatus. The PCR machine 2 provides the motive power to the preparation apparatus. A sample to be analysed, in a liquid or semi-solid state is added to an inlet 4 at the upper end of the apparatus. The apparatus extracts the nucleic acid from the sample and prepares it into a form suitable for PCR analysis, dispensing it into a vertically arranged transparent cuvette 5 at the lower end of the apparatus. The cuvette 5 with the prepared sample is then lowered from the preparation apparatus into the PCR machine 2 through a suitable opening (not shown) so that the PCR machine can carry out the amplification and analysis in the usual way while the preparation apparatus remains in position on the PCR machine. After the analysis has been completed, the cuvette 5 is withdrawn back up into the preparation apparatus so that the apparatus and sample can be disposed of safely. A new sample can then be tested using a new sample preparation apparatus.

Figure 2A:
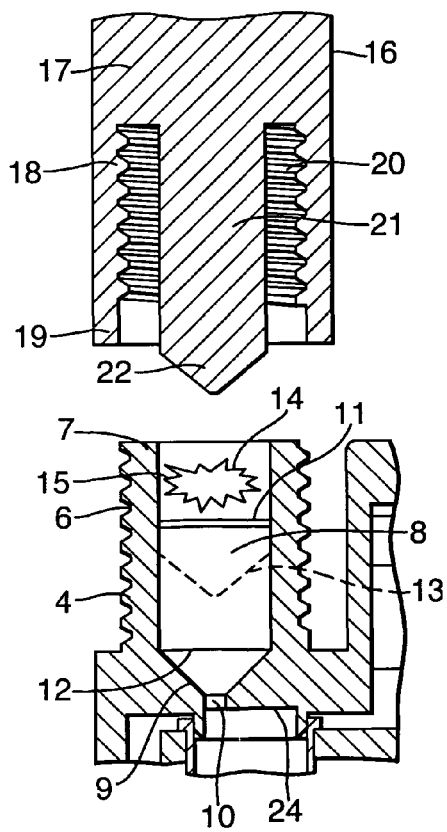
FIGS. 2A to 2C are cross-sectional views of the inlet of the apparatus at three different stages.
Figure 2B:
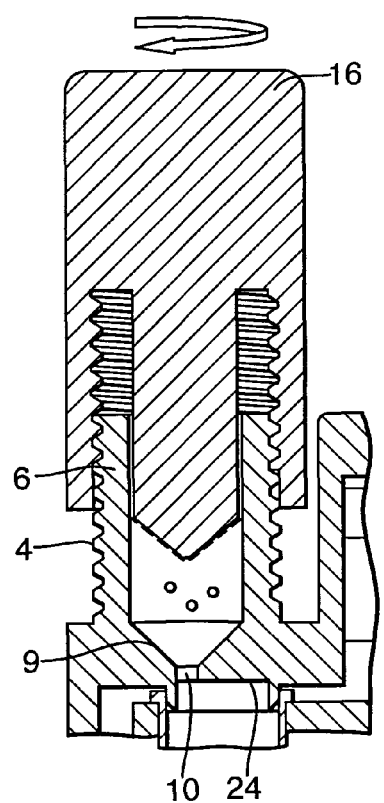
Figure 2C:
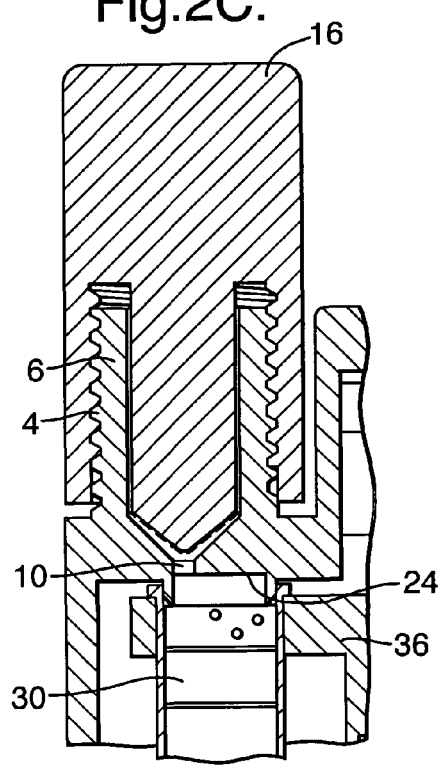
Figure 4:
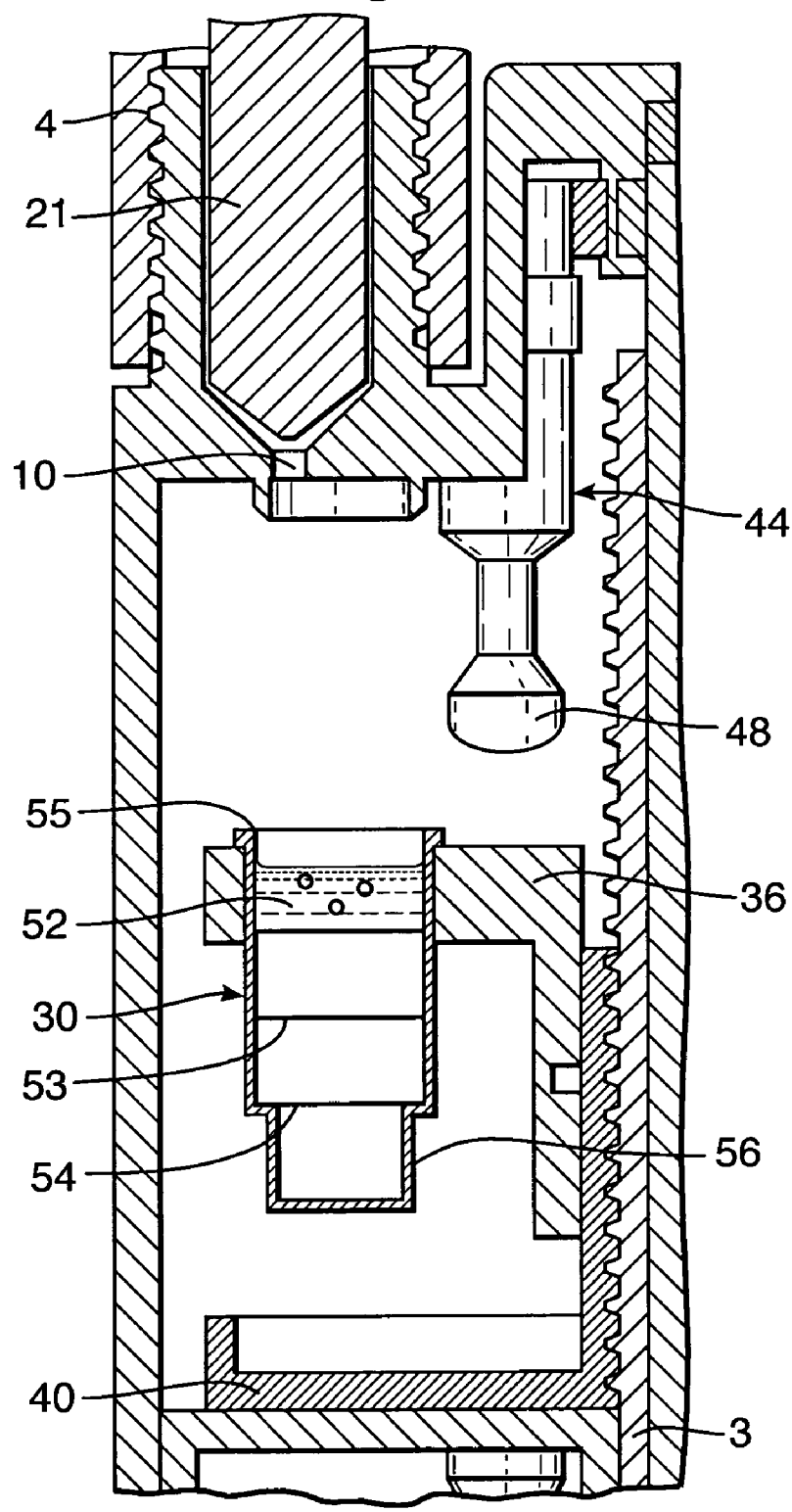
FIG. 4 is a cross-sectional view of a part of the apparatus at an initial stage of operation.

The construction and operation of the apparatus will now be described in greater detail, initially with reference to FIGS. 2A to 2C. The inlet 4 of the apparatus is provided by a cylindrical, externally screw-threaded boss 6 positioned to one side of the casing 1 at its upper end. The boss 6 is arranged vertically with an open upper end 7 and an internal cylindrical recess 8 having a tapered lower end 9 and an outlet opening 10. The recess 8 contains a lysis solution between upper and lower rupturable, foil seals 11 and 12. The recess 8 also contains a sieve member in the form of a grill 13 of conical shape mounted about half way along the recess, between the two foil seals 11 and 12. The upper seal 11 is spaced from the upper end 7 of the boss 6 so as to provide an open cavity 14, above the seal into which the sample 15 can be placed. The inlet 4 also includes a maceration member in the form of a closure cap 16, which serves the dual function of macerating the sample 15 and of closing the inlet. The cap 16 is of cylindrical shape having a closed upper end 17 and an outer sleeve 18 with an open lower end 19 and a screw-threaded internal surface 20. The screw-threaded internal surface 20 on the cap 16 is adapted to engage with the external screw thread on the boss 6. The cap 16 also has a central maceration rod 21 projecting axially downwardly and provided with a conical lower end surface 22. The external diameter of the rod 21 is such that the rod is a close sliding fit within the recess 8 of the boss 6. The conical lower end 22 of the rod 21 has the same shape as the upper surface of the grill 13 and the tapered lower end 9 of the recess 8.

In operation, the sample 15 is added to the open cavity 14 in the recess 8 above the upper seal 11. The sample remains above the seal 11 until the cap 16 is screwed onto the boss 6 and the lower end 22 of the rod 21 ruptures the upper seal enabling the sample to mix with the lysis solution. The lysis solution is effective to disrupt the cells of the sample and release nucleic acid, DNA or RNA. Where the sample 15 is a liquid this lysis stage will start to happen immediately the sample contacts the lysis solution and it will flow freely through the grill 13. Where the sample 15, however, is a semi-solid, such as a biological tissue sample, it remains above the grill 13. However, as the user screws the cap 16 fully down onto the boss 6, the lower surface 22 of its rod 21 rotates and pushes down against material collecting on the grill 13, thereby forcing it through the grill and consequently macerating the material into small pieces, as shown in FIG. 2B. The grill 13 is constructed such as to be sufficiently rigid to withstand the pressure exerted by the passage of semi-solid sample material through it. The lower surface 22 of the rod 21 contacts the upper surface of the grill after all the sample material 15 has been pushed through. Further twisting of the cap 16 increases force on the grill 13 until it exceeds its fracture limit and the grill breaks to allow the rod 21 to move further down the recess. As this happens, pressure builds up on the lysis and sample mixture below the rod 21 until this exceeds the breaking limit of the lower seal 12. The mixture then flows out of the outlet 10 and a filter 24 at the lower end of the inlet 4. This continues until the cap 16 has been screwed fully down and all the sample material has been pushed out of the outlet 10 by the lower end 22 of the rod 21, as shown in FIG. 2C. The filtered mixture of the lysis solution and sample flows into a first reaction vessel 30 below the outlet 10.

With reference now to FIGS. 3A and 3B, the reaction vessel 30 is one of three reaction vessels 30 to 32 mounted around the edge of a first, upper, circular support plate 36. The Figures show six stations around the upper plate 36 but, in this application three of these stations are blank, although in other applications additional reaction vessels could be provided at the blank stations. The plate 36 has a central aperture 37 through which extends the drive shaft 3. The drive shaft 3 has a portion 38 with an external screw thread, which cooperates with the aperture 37 in the plate 36 such that the plate moves up and down and is indexed angularly around the apparatus step by step as the drive shaft rotates. As can be seen from FIGS. 3A and 3B, the apparatus also includes a circular, lower, cuvette support plate 40 mounted on the drive shaft 3 below the upper support plate 36. The lower plate 40 is constrained not to rotate but to move axially up and down only. The plate 40 supports a cuvette assembly 41, which will be described in detail later.

Figure 5:
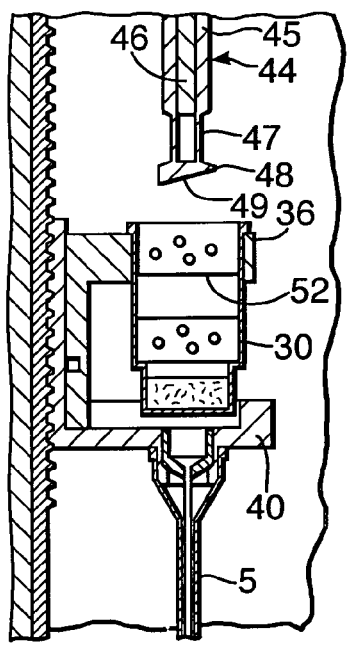
FIGS. 5 to 19 are cross-sectional views of parts of the apparatus at different stages of operation.
Figure 6:
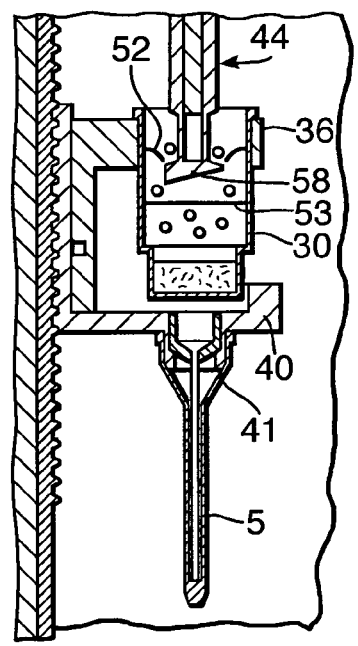
Figure 7:
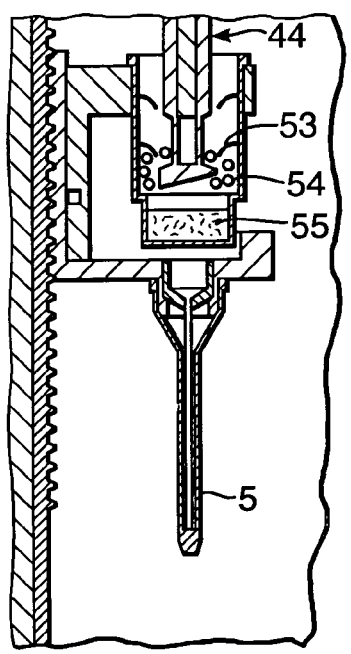
Figure 8:
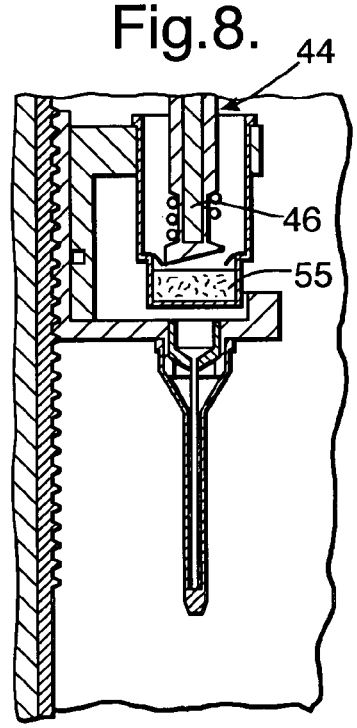

A magnetic transfer assembly 42 is mounted above the upper plate 36 at the upper end of the casing 1; this is used to transfer material, between vessels using magnetic beads in the vessels. The transfer assembly 42 is coupled to the upper end of the drive shaft 3 by a linkage 43. The transfer assembly 42 includes a magnetic plunger 44, as shown in section in FIGS. 5 to 19, which is rotatable by the linkage 43 about its axis. The plunger 44 comprises an outer plastics sheath 45 and an inner permanent magnet core 46 that is slidable axially up and down relative to the sheath. The sheath 45 is profiled at its lower end to provide a collection region 47 of reduced external diameter and wall thickness, and a lower, head portion 48. The head portion 48 has an inclined lower surface 49, which serves two purposes, namely to facilitate smooth piercing of foil seals on various reaction vessels and to increase turbulence when the plunger is rotated with the head immersed in a fluid so as to create an enhanced stirring effect. The magnet core 46 has a cylindrical shape and is moved by the linkage 43 up and down relative to the outer sheath 45 between a first raised position, as shown in FIGS. 5, 6 and 7, where the lower end of the magnet is level with the upper end of the collection region 47, to a second, lowered position, as shown in FIGS. 8 to 11, where the lower end of the magnet is level with the upper end of the enlarged head 48. The thickness and material of the sheath 45 is arranged such that, when the magnet 46 is in the raised position, there is insufficient magnetic field flux at the surface of that part of the plunger immersed in the reaction vessels to attract or retain magnetic beads used in the transfer process. This state of the plunger 44 can, therefore, be regarded as the "release" state. When, however, the magnet 46 is fully lowered into the sheath 45, the wall thickness in the collection region 47 is such that the magnetic field flux on the outside surface is sufficient to collect all magnetic beads within the reaction vessel. In this position of the magnet 46 the plunger 44 is in a "collect" state. The thickness of the head 48 is such that there is insufficient magnetic field flux at its outer surface, even when the magnet 46 is in its lowered position, to retain magnetic beads on its surface. Magnetic beads collected on the plunger 44 are, therefore, confined to the collection region 47 behind the head 48. Although the plunger 44 is rotatable it cannot move up and down so instead the reaction vessels 30 to 32 are raised up and down, by raising the upper support plate 36 up and down, to immerse the plunger in the vessels as required. Initially, during the introduction of the sample to the inlet 4, the upper support plate 36 is in a raised position and the plunger 44 is aligned with a cut-away recess 50 in one side of the plate.

The different steps in operation of the sample preparation apparatus will now be described with reference to FIGS. 4 to 19.

As soon as the cap 16 has been fully screwed onto the inlet 4, the PCR machine 2 is initiated to start the drive to the shaft 3 in the sample preparation apparatus. As the shaft 3 rotates, it starts to lower the upper support plate 36 from the raised position shown in FIG. 2C to the position shown in FIG. 4 where the plate and vessel 30 are in a lowered position. It can be seen from FIG. 4 that the upper surface of the support plate 36 is now spaced below the lower end 48 of the plunger 44.

Figure 9:
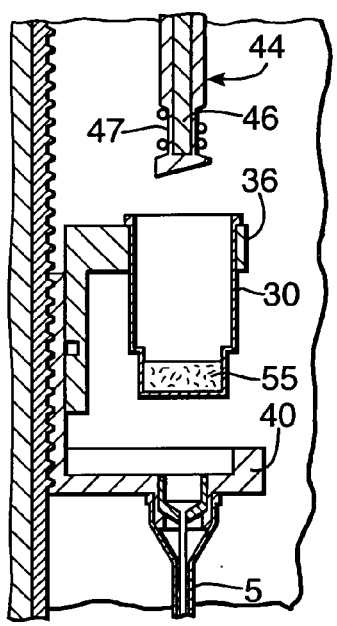

The reaction vessel 30 has three rupturable, foil seals 52, 53 and 54 at spaced locations along the length of the vessel. The first, upper seal 52 is spaced from the open upper end 55 of the vessel 30 so that the mixture of the lysis solution and sample is held initially in the upper part of the vessel above this seal. The upper support plate 36 is rotated clockwise (when viewed from above) through about 50° to index the first reaction vessel 30 around from its initial position beneath the inlet 4 to a second position beneath the plunger 44. The magnet 46 in the plunger 44 is positioned in its raised state initially. As shown in FIG. 5, continued rotation of the drive shaft 3 causes the lower plate 40 to rise and lift up the upper support plate 36 relative to the plunger 44 until, as shown in FIG. 6, the lower edge of the plunger head 48 enters the reaction vessel 30 and pierces the first, upper foil seal 52. Between the first and second seals 52 and 53 the vessel 30 contains a second lysis solution so this mixes with the mixture of the sample and the first lysis solution. The mixing is promoted by rotation of the plunger 44, which acts to stir the mixture together. Further rotation of the drive shaft 3 causes the lower plate 40 to rise further until the lower end of the plunger 44 pierces the second foil seal 53. The space below the second seal 53 contains a mixture of magnetic beads (such as of the kind sold by Bio-Nobile Oy) and a buffer solution. The magnetic beads are coated with a substance selected to bind with nucleic acid, DNA or RNA. The plunger continues to rotate to encourage mixing. After mixing has been completed, the plunger 44 stops rotating and the magnet 46 is lowered within the sheath 45 so that the magnetic beads with the nucleic acid substance bound to them are attracted to the collection region 47 of the plunger. Further rotation of the drive shaft 3 causes the upper plate 36 and reaction vessel 30 to move further up until the lower end of the plunger 44 pierces the third foil 54. Below the third foil 54 the vessel 30 contains a mass of absorbent material 55 so that fluid in the vessel is absorbed into this material, leaving the magnetic beads clinging to the plunger 44. The enlarged head 48 and recessed nature of the collection region 47 reduces the risk that beads will be dislodged from the plunger 44 as it passes through sealing foils. The next step is that the lower plate 40 and upper plate 36 move down, leaving the lower end of the plunger 44 clear above the upper surface of the upper plate, as shown in FIG. 9.

Figure 10:
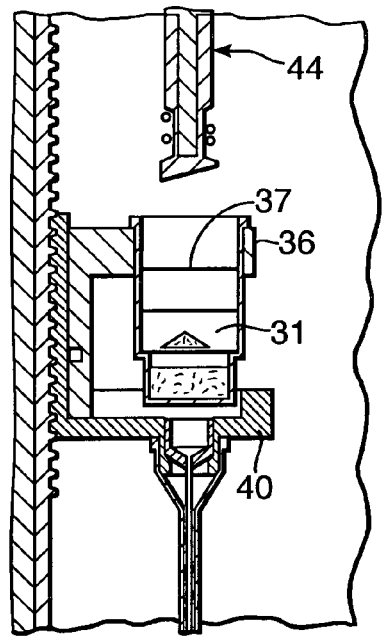
Figure 11:
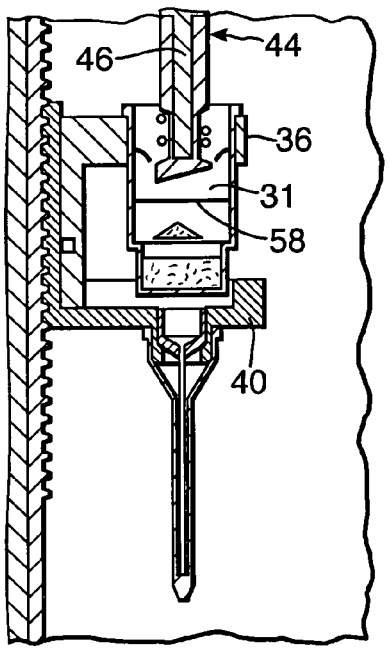
Figure 12:
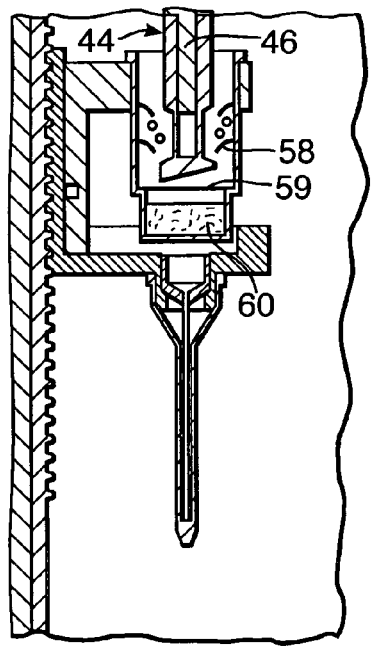
Figure 13:
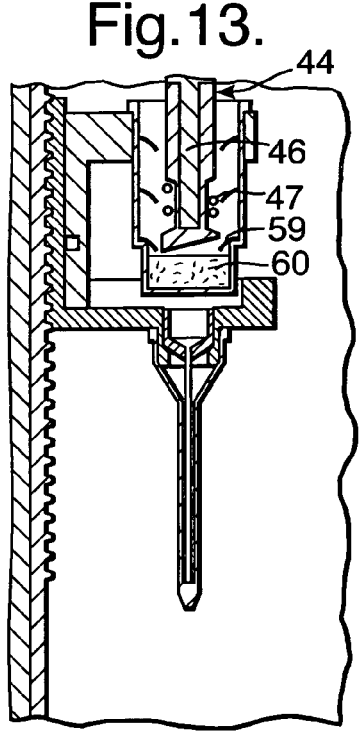
Figure 14:
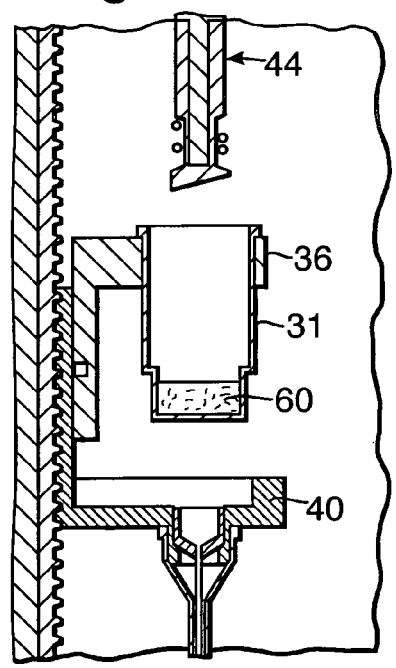

The upper support plate 36 next rotates one stage further clockwise so that the second reaction vessel 31 is located beneath the plunger 44, as shown in FIG. 10. The lower plate 40 rises causing the upper plate 36 also to rise and the lower end of the plunger 44 to pierce an upper foil seal 37 in the reaction vessel 31, as shown in FIG. 11. The vessel 31 contains a buffer solution below the upper seal 37 and above a second seal 58. The magnet 46 in the plunger 44 rises to its release condition to allow the beads to come away from the plunger and mix with the buffer solution. Rotation of the plunger 44 encourages mixing and the beads to be released. The upper plate 36 continues to rise until the lower end of the plunger 44 ruptures the second seal 58 as shown in FIG. 12. In the space between the second and third seals 58 and 59 the vessel contains a DNASE enzyme, which is mixed with the beads and buffer solution. When mixing has been completed, the magnet 46 is lowered again in the plunger 44 so that the beads are attracted back to the collection region 47. The reaction vessel 31 is raised further until the third seal 59 is broken, allowing the waste solution to drain into the space below the seal, which contains an absorbent material 60, as shown in FIG. 13. Next, as shown in FIG. 14, the lower plate 40 lowers, allowing the upper plate 36 to lower and leaving the lower end of the plunger 44 above the upper surface of the upper plate 36 with the beads attracted to its surface.

Figure 15:
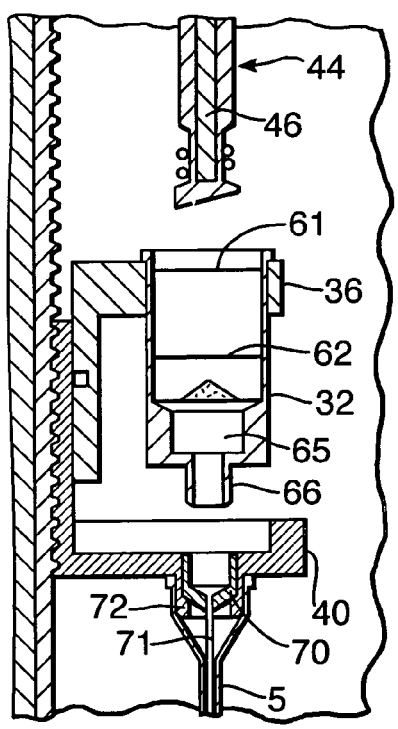
Figure 16:
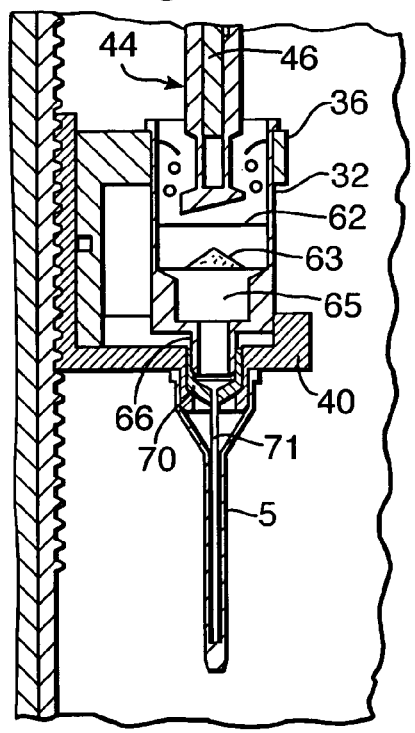
Figure 17:
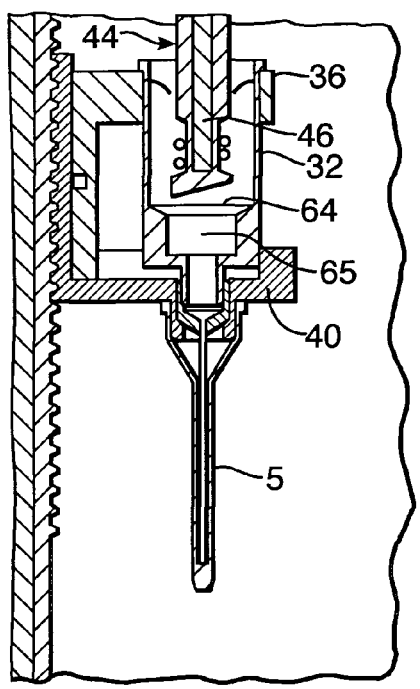

The upper support plate 36 now rotates one more step to bring the third and final reaction vessel 32 into alignment below the plunger 44, as shown in FIG. 15. The lower plate 40 rises to lift the upper plate 36 and reaction vessel 32 until the lower end of the plunger 44 pierces a foil seal 61 close to the upper end of the vessel and enters a space above a second seal 62 containing a buffer or washing solution. The plunger magnet 46 now rises so that the beads are released into the buffer solution, the plunger 44 rotating to promote mixing and release of the beads, as shown in FIG. 16. The buffer solution is effective to separate the nucleic acid, DNA or RNA bound to the beads and return it to solution in the buffer. The magnet 46 now lowers again in the plunger 46 so that the washed beads, without the bound nucleic acid, are attracted to the collection region 47. Next, as shown in FIG. 17, the vessel 32 is raised further so that the plunger 44 breaks the second foil seal 62 and allows the buffer solution to mix with a selected reverse transcription (RT) reagent 63 in the space between the second seal and a third seal 64. The upper plate 36 continues to rise so that the plunger 44 pierces the third seal 64 and allows the solution to drain into a chamber or barrel 65 at the lower end of the vessel 32.

Figure 18:
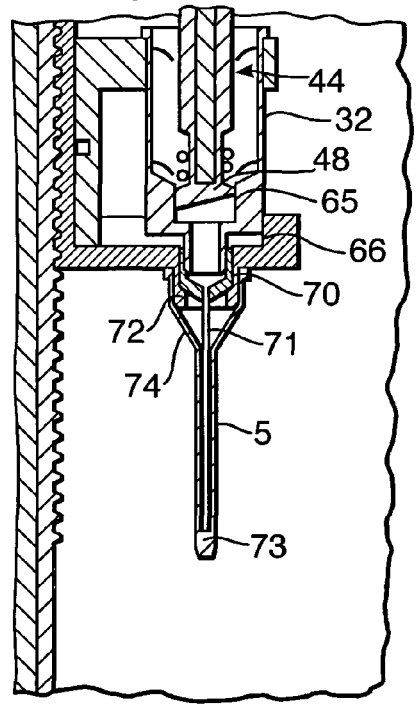

The chamber 65 at the lower end of the final reaction vessel 32 opens through an outlet nose 66. When the lower plate 40 is in a raised position, as shown in FIGS. 16, 17 and 18, the outlet nose 66 of the reaction vessel 32 enters and seals with a hub 70 of a fine, hollow, metal filling needle 71. The hub 70 of the needle 71 is loosely and releasably mounted to extend through the lower plate 40 and is aligned below the plunger 44. The needle 71 extends within the cuvette 5, which is secured fixedly to a spigot 72 projecting from the underside of the lower plate 40. The cuvette 5 has a circular section, is elongate with a relatively small diameter; it has a closed lower end 73 and an open upper end 74. The cuvette 5 is made of a material that is transparent to the optical radiation used in the PCR analysis process and, in this respect, it may be of a glass or a transparent plastics material. The external diameter of the filling needle 71 is less than the internal diameter of the cuvette 5 so that there is a clearance between the two. The length of the filling needle 71 is such that it extends close to the lower end 73 of the inside of the cuvette 5 to allow fluid to flow out of the lower end of the needle into the cuvette. This arrangement avoids the need to centrifuge the cuvette to ensure the fluid flows to its lower end, such as described in US2005064582.

The chamber 65 at the lower end of the final reaction vessel 32 has a reduced internal diameter closely matched to the external diameter of the head 48 of the plunger 44. In this way, as the final reaction vessel 32 continues to rise, the head 48 of the plunger 44 enters the chamber 65 as a close sliding fit and acts to pump fluid in the chamber out of the outlet nose 66 in the manner of a plunger in the barrel of a syringe, as shown in FIG. 18. The small internal diameter of the filling needle 71 restricts free flow of fluid through it thereby making a plunger necessary although, if an alternative less restricted outlet were used, it might not be needed.

Figure 19:
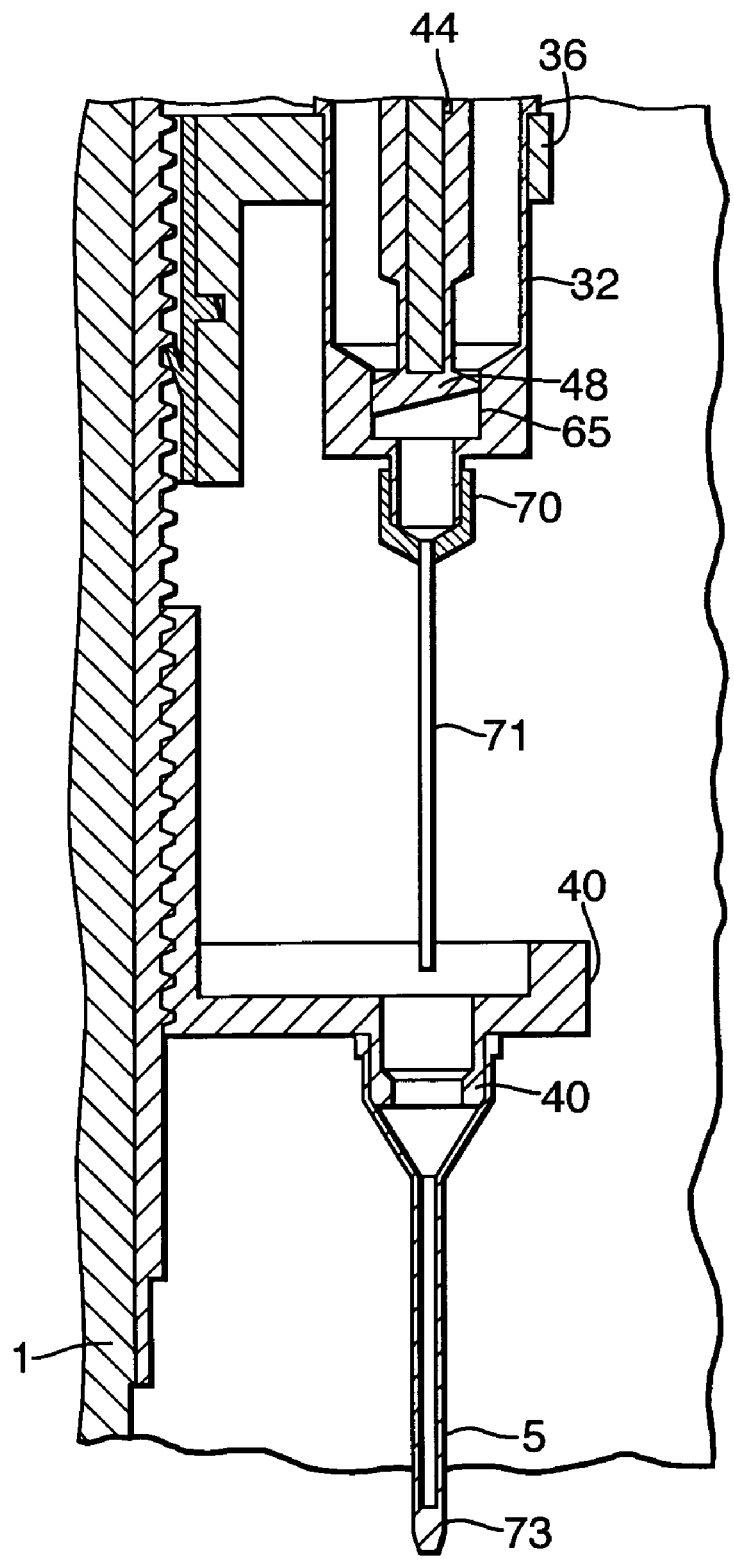

Continued rotation of the drive shaft 3 causes the lower support plate 40 to move down so as to separate the filled cuvette 5 from the filling needle 71, which remains attached to the nose 66 of the final reaction vessel 32, as shown in FIG. 19. The lower support plate 40 continues to fall, moving the lower end of the cuvette 5 below the lower end of the casing 1 and into a sample opening in the upper surface of the PCR machine 2. It is necessary to extract the needle 71 before PCR analysis because it is made of metal and is, therefore, opaque and would prevent free passage of optical radiation through the cuvette. If, however, the filling needle were made of a transparent material, such as a glass or plastics it might be possible to leave the filling needle in the cuvette during analysis.

Various modifications are possible to the apparatus. For example, there may be arrangements other than using magnetic beads to transfer substance material between different reaction vessels. When magnetic beads are used these could be transported in other ways, such as by using an electromagnet, although this would have the disadvantage of requiring electrical power. It is not essential that the apparatus be mounted on and driven by a PCR machine although this is an advantage. A different embodiment of the sample preparation apparatus could be a stand-alone device driven by its own motor, or by manual means, to provide a prepared sample for analysis by a separate PCR machine.

The present invention provides apparatus that can be used readily to prepare biological material in the field for analysis with little training. The sample preparation apparatus is single-use and disposable so that different samples can be treated in the same PCR machine in quick succession.

The invention claimed is:

1. Sample preparation apparatus for preparing a biological sample and dispensing it into an elongate transparent cuvette suitable for PCR amplification and analysis, characterised in that the cuvette has an open upper end and a closed lower end, that the apparatus includes a needle extending into the lower end of the cuvette such as to provide clearance between the outside of the needle and the inside of the cuvette, and that the apparatus is arranged to dispense the PCR sample into the upper end of the needle so that it fills the cuvette from its lower end.

2. A sample preparation apparatus comprising:
 i) a maceration member having threads to engage with a boss that has corresponding threads, said boss defining a recess for holding a sample, wherein a first seal is disposed within said boss and is configured to rupture responsive-to rotation of said maceration member or said boss;
 ii) a first reaction vessel configured to receive said sample from said boss;
 iii) a final reaction vessel configured to contain sample material;
 iv) a transfer assembly configured to transfer sample material between reaction vessels; and
 v) a needle configured to pass said sample material contained in said final reaction vessel to a cuvette so said sample material is dispensed at a closed end of said cuvette so as to fill said cuvette from said closed end.

3. The sample preparation apparatus of claim 2, further comprising a second seal disposed in said recess, said second seal configured to rupture after additional rotation of said maceration member or said boss.

4. The sample preparation apparatus of claim 3, wherein said boss contains a substance to disrupt cells in said sample to release nucleic acid, said substance being retained in said boss by said first seal and said second seal.

5. The sample preparation apparatus of claim 4, wherein said substance comprises a lysis solution.

6. The sample preparation apparatus of claim 4, wherein said boss is configured to dispense said sample to said first reaction vessel responsive to rupture of said second seal.

7. The sample preparation apparatus of claim 6, wherein said maceration member is configured to mix said sample in said recess prior to rupture of said second seal.

8. The sample preparation apparatus of claim 3, wherein said first seal and said second seal comprise foil seals.

9. A sample preparation apparatus, comprising:
 i) a needle configured to fill a cuvette, wherein said cuvette has an open upper end and a closed lower end, wherein said needle is configured to fill said cuvette from said cuvette's closed end, said needle extending between said cuvette's open end and said cuvette's closed end;
 ii) a needle hub attached to said needle; and
 iii) a reaction vessel configured to contain a biological sample that has been treated to disrupt cells in said biological sample to release nucleic acid, said reaction vessel being configured to dispense said biological sample to said needle, wherein said reaction vessel comprises an outlet nose which is inserted into, and releasable sealed with, said needle hub.

10. The sample preparation apparatus of claim 9, further comprising a buffer or wash solution and a seal disposed in said reaction vessel, wherein said buffer or wash solution is held above said seal in said reaction vessel, and wherein said seal is configured to be ruptured.

11. The sample preparation apparatus of claim 9, further comprising a seal disposed in said reaction vessel, wherein said seal is configured to be ruptured and is disposed in said reaction vessel to prevent said biological sample from being dispensed to said needle prior to rupture of said seal.

12. The sample preparation apparatus of claim 9, further comprising:
 iii) a first seal and second seal with a wash or buffer solution disposed in said reaction vessel between said first and second seals, wherein said first seal and said second seal are configured to be ruptured; and
 iv) a third seal disposed in said reaction vessel configured to prevent of said biological sample to said needle prior to rupture of said third seal.

13. A method comprising:
 i) breaking a first seal to cause lysis solution to mix with a biological sample to disrupt cells in said biological sample to release nucleic acids from the cells;
 ii) breaking a second seal to dispense at least a portion of said nucleic acids into a needle; and
 iii) filling a cuvette with a solution including said nucleic acids from a cuvette's closed end.

14. The method of claim 13, further comprising, rotating a cap on a reaction vessel to cause a rod on said cap to break said first seal.

15. The method of claim 14, further comprising mixing said biological sample, wherein said mixing is at least partially accomplished by said rod responsive to rotation of said cap.

* * * * *